United States Patent
Jung

(10) Patent No.: US 10,206,760 B2
(45) Date of Patent: Feb. 19, 2019

(54) ORTHODONTICS AND TEMPOROMANDIBULAR JOINT BALANCING APPLIANCE

(71) Applicant: Soo Chang Jung, Seoul (KR)

(72) Inventor: Soo Chang Jung, Seoul (KR)

( * ) Notice: Subject to any disclaimer, the term of this patent is extended or adjusted under 35 U.S.C. 154(b) by 181 days.

(21) Appl. No.: 14/277,417

(22) Filed: May 14, 2014

(65) Prior Publication Data
US 2014/0342299 A1 Nov. 20, 2014

(30) Foreign Application Priority Data

May 14, 2013 (KR) .................. 10-2013-0054195
Jun. 20, 2013 (KR) .................. 10-2013-0071173

(51) Int. Cl.
*A61C 7/08* (2006.01)
*A61F 5/56* (2006.01)
*A61C 7/36* (2006.01)

(52) U.S. Cl.
CPC ............ *A61C 7/08* (2013.01); *A61F 5/566* (2013.01); *A61C 7/36* (2013.01)

(58) Field of Classification Search
CPC .......... A61F 5/56; A61F 5/566; A63B 71/085; A63B 2071/086; A63B 2071/088; A61C 7/08; A61C 5/14
USPC ...................... 433/6, 35, 215–216
See application file for complete search history.

(56) References Cited

U.S. PATENT DOCUMENTS

| | | | | |
|---|---|---|---|---|
| 2,257,709 A | * | 9/1941 | Anderson | A61C 17/00 128/861 |
| 3,236,235 A | * | 2/1966 | Jacobs | A63B 71/085 128/862 |
| 3,319,626 A | * | 5/1967 | Lindsay | A63B 71/085 128/861 |
| 3,864,832 A | * | 2/1975 | Carlson | A61O 5/90 128/862 |
| 5,163,840 A | * | 11/1992 | Bourke | A61C 7/08 433/24 |
| 5,931,164 A | * | 8/1999 | Kiely | A63B 71/085 128/859 |
| 6,071,121 A | * | 6/2000 | Simon | A61C 7/08 433/37 |
| 8,091,555 B2 | * | 1/2012 | Morgan | A63B 71/085 128/859 |
| 8,578,940 B1 | * | 11/2013 | Van Essen | A61O 5/90 128/859 |
| 2010/0196837 A1 | * | 8/2010 | Farrell | A61C 7/08 433/6 |

(Continued)

FOREIGN PATENT DOCUMENTS

KR 2020070008527 5/2007
KR 100926483 B1 11/2009
WO WO 2006/099213 A2 * 9/2006

*Primary Examiner* — Kari Rodriquez
*Assistant Examiner* — Camtu Nguyen
(74) *Attorney, Agent, or Firm* — Lucas & Mercanti, LLP

(57) ABSTRACT

The present invention relates to an orthodontics and temporomandibular joint balancing appliance, particularly to an orthodontics and temporomandibular joint balancing appliance, which eliminates asymmetric imbalance of a temporomandibular joint caused by pressure applied to upper incisor teeth and lower incisor teeth, thereby cushioning every teeth occlusion and blocking nervous system compression, so as to minimize teeth damage and improve wearing comfortness.

1 Claim, 9 Drawing Sheets

(56) References Cited

U.S. PATENT DOCUMENTS

2013/0312655 A1\* 11/2013 Gravelle .............. A63B 71/085
  116/216

\* cited by examiner

A-A'

B-B'

ORTHODONTICS AND TEMPOROMANDIBULAR JOINT BALANCING APPLIANCE

CROSS-REFERENCE TO RELATED APPLICATIONS

This application claims the priority of Korean Patent Application No. 10-2013-0054195 filed on May 14, 2013, and of Korean Patent Application No. 10-2013-0071173 filed on Jun. 20, 2013, the contents of each of which are incorporated by reference herein.

FIELD OF THE INVENTION

The present invention relates to an orthodontics and temporomandibular joint balancing appliance, particularly to an orthodontics and temporomandibular joint balancing appliance, which eliminates asymmetric imbalance of a temporomandibular joint caused by pressure applied to upper incisor teeth and lower incisor teeth, thereby cushioning every teeth occlusion and blocking nervous system compression, so as to minimize teeth damage and improve wearing comfortness.

BACKGROUND OF THE INVENTION

In general, a TemporoMandibular Joint (TMJ) is a ginglymoarthrodial joint, referring to its dual compartment structure, which serves as a central axis of mandibular movements during chewing (masticatory movement). The TMJ makes a rotational (hinge) movement and a sliding movement for opening and closing mouth, and plays a significant role in chewing and talking. The TMJ has a temporal bone and a jaw bone called a mandible.

The TMJ is an essential part of the body in which nine of 12 cranial nerves are extended and a large number of blood vessels, lymphatic vessels, and nerves are distributed. TMJ imbalance may cause general symptom. In particular, the TMJ imbalance may cause subluxation of the cervical vertebrae 1 and 2 and may break muscle balance around the neck, thereby causing a wide range of general symptoms including headache, dizziness, circulation disorders, otolaryngological disorders, urologic disorders, respiratory disorders and growth disorders as well as disorders in the central nervous system, spinal joint and musculoskeletal system. This TMJ imbalance may be caused by movements such as continuous moving, chewing, swallowing and talking, and stress.

Therefore, importance of the TMJ is increasing and the TMJ is under active study and research. Also, many TMJ protection appliances such as a TMJ correction pad, a mouthpiece, an occlusal balancing appliance and a correction device have been invented.

Conventional technologies disclosed in Korean Patent Registration No. 10-0926483 is characterized in that, in a temporomandibular joint balancing appliance, the first base portion for receiving incisors is separately formed from the second base portion and the third base portion for receiving molars, thereby enhancing wearing comfortness of users and minimizing teeth pain when wearing. However, the parts for incisors and molars are separated, thereby a joint part may be wobbled when occluding.

This causes inconvenience by forcing users to wear for a long time because it is difficult to be fixed to teeth. Therefore, it is designed to be structurally impossible to solve the TMJ imbalance.

Further, Korean Patent Registration No. 10-200982 about a temporomandibular joint correction pad for application to gum of upper incisor teeth, Korean Patent Registration No. 10-200983 about a temporomandibular joint correction pad for application to gum of lower incisor teeth and the like are characterized by using fluid for correcting disk of the TMJ, and installing thereof to gum of lower incisor teeth or upper incisor teeth. However, there are problems that the correction pads are applied to lower incisor teeth or upper incisor teeth, thereby easily detached from teeth because it is difficult to fix them to gum when wearing, and wearing comfortness is remarkably deteriorated by movement of the fluid when teeth are gathered.

SUMMARY OF THE INVENTION

The present invention is objected to provide an orthodontics and temporomandibular joint balancing appliance having novel structure, which is inserted between teeth and to gum extended from teeth, and stimulates teeth and maintains balance of a temporomandibular joint at the same time, so as to minimize imbalance of the temporomandibular joint.

In order to accomplish one object of the present invention, provided is an orthodontics and temporomandibular joint balancing appliance comprising:

i) a horizontal supporting portion formed as the oral cavity shape, in which upper incisor teeth are accommodated in the upper part and lower incisor teeth are accommodated in the lower part;

ii) an upper part outer wall, which is extended to the direction perpendicular to an upper part outer rim of the horizontal supporting portion and supports the outer part of the upper incisor teeth;

iii) an upper part inner wall, which is extended to the direction perpendicular to an upper part inner rim of the horizontal supporting portion and supports the inner part of the upper incisor teeth;

iv) a lower part outer wall, which is formed along a lower part outer rim of the horizontal supporting portion and supports the outer part of the lower incisor teeth;

v) a lower part inner wall, which is formed along a lower part inner rim of the horizontal supporting portion and supports the inner part of the lower incisor teeth;

vi) an upper gum protecting portion, which is extended from the upper part outer wall toward gum and protects gum; and vii) a lower gum protecting portion, which is extended from the lower part outer wall toward gum and protects gum.

In the present invention, the upper part outer wall may comprise an upper part outer protrusion at the side faced the upper incisor teeth.

In the present invention, the upper part inner wall may comprise an upper part inner protrusion at the side faced the upper incisor teeth.

In the present invention, the upper gum protecting portion may comprise a first upper part groove for protecting gum, enhancing fixability with teeth and enabling easier removal.

In the present invention, the upper part inner wall may comprise a second upper part groove for enhancing fixability with teeth and enabling easier removal.

In the present invention, the lower part outer wall may comprise a lower part outer protrusion at the side faced the lower incisor teeth.

In the present invention, the lower part inner wall may comprise a lower part inner protrusion at the side faced the lower incisor teeth.

In the present invention, the upper part outer protrusion or the upper part inner protrusion may be formed at the ratio of at least one per tooth.

In the present invention, the lower part outer protrusion or the lower part inner protrusion may be formed at the ratio of at least one per tooth.

Advantageous Effects of the Invention

The present invention has effects of eliminating asymmetric imbalance of a temporomandibular joint caused by pressure applied to upper incisor teeth and lower incisor teeth, thereby cushioning every teeth occlusion and blocking nervous system compression, so as to minimize teeth damage and improve wearing comfortness.

Further, the present invention comprising gum protecting portions extended from the upper and lower outer walls of the appliance has an effect of improving pleasant wearing comfortness by minimizing foreign bodies between teeth and gum and foreign body sensation.

Further, the present invention can improves wearing comfortness of users and maximize teeth fixation by fixing teeth not to be separated through protrusions protruded from the upper and lower inner walls and the upper and lower outer walls of the appliance.

BRIEF DESCRIPTION OF DRAWINGS

The above and other objects and features of the present invention will become apparent from the following description of the invention taken in conjunction with the following accompanying drawings, which respectively show.

DESCRIPTION OF SYMBOLS

Figure 1:
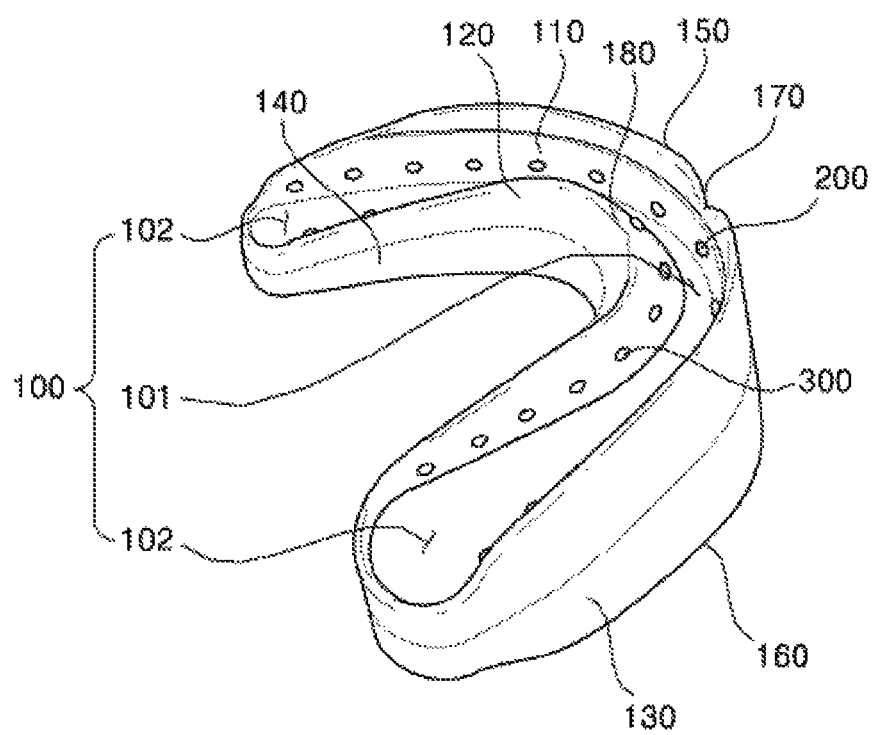
FIG. 1 represents a perspective view of the orthodontics and temporomandibular joint balancing appliance according to one embodiment of the present invention.

100: Horizontal supporting portion
101: Anterior teeth
102: Posterior teeth
110: Upper part outer wall
120: Upper part inner wall
130: Lower part outer wall
140: Lower part inner wall
150: Upper gum protecting portion
160: Lower gum protecting portion
170: First upper part groove
180: Second upper part groove
200: Upper part outer protrusion
300: Upper part inner protrusion
400: Lower part outer protrusion
500: Lower part inner protrusion

DETAILED DESCRIPTION OF THE INVENTION

The above and other aspects, features, and advantages of the invention will become apparent from the detailed description of the following embodiments in conjunction with the accompanying drawings. It should be understood that the present invention is not limited to the following embodiments and may be embodied in different ways, and that the embodiments are provided for complete disclosure and a thorough understanding of the invention to those skilled in the art.

Hereinafter, the present invention will be described in detail with reference to the accompanying drawings.

Figure 2:
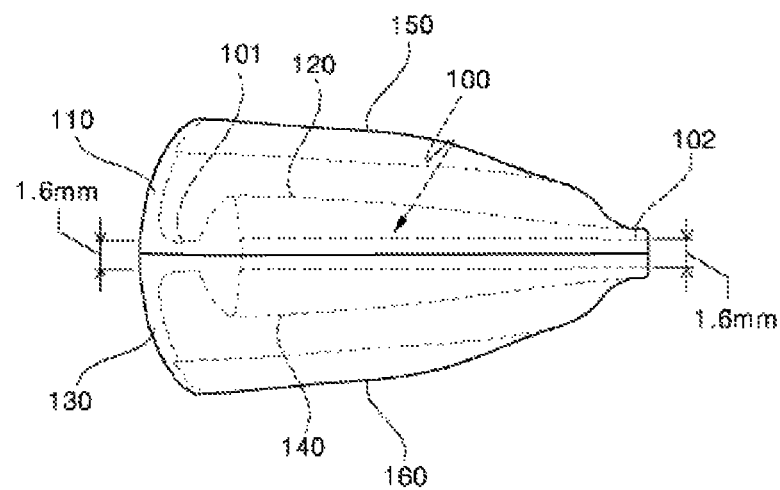
FIG. 2 represents a side view of the orthodontics and temporomandibular joint balancing appliance according to one embodiment of the present invention.
Figure 3:
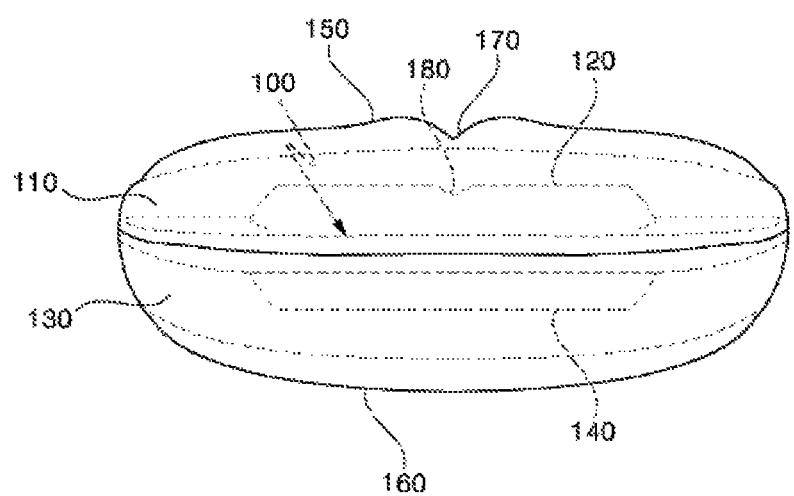
FIG. 3 represents a front view of the orthodontics and temporomandibular joint balancing appliance according to one embodiment of the present invention.
Figure 4:
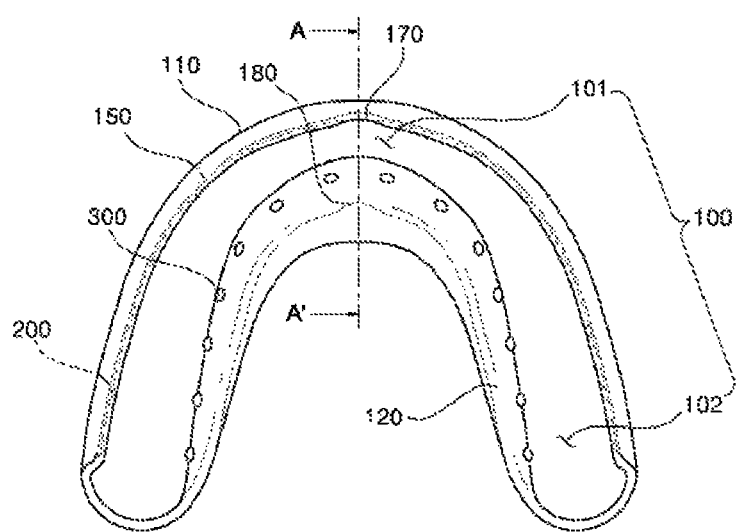
FIG. 4 represents a floor plan of the orthodontics and temporomandibular joint balancing appliance according to one embodiment of the present invention.
Figure 5:
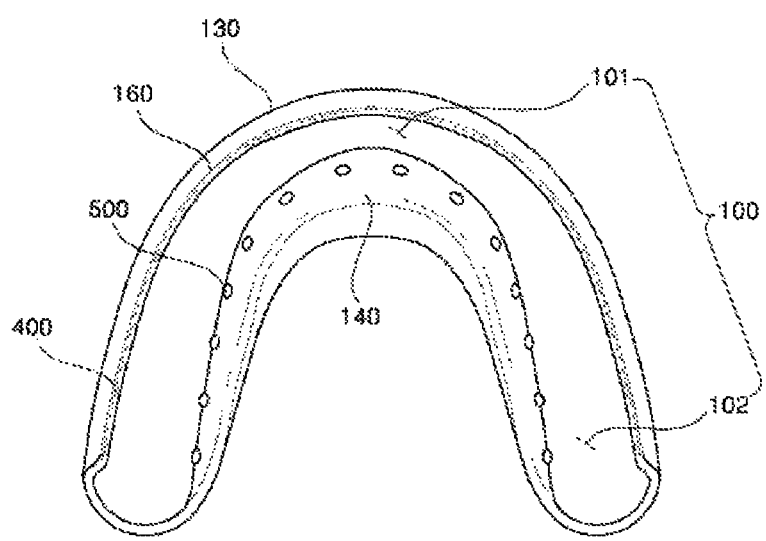
FIG. 5 represents a base drawing of the orthodontics and temporomandibular joint balancing appliance according to one embodiment of the present invention.
Figure 6:
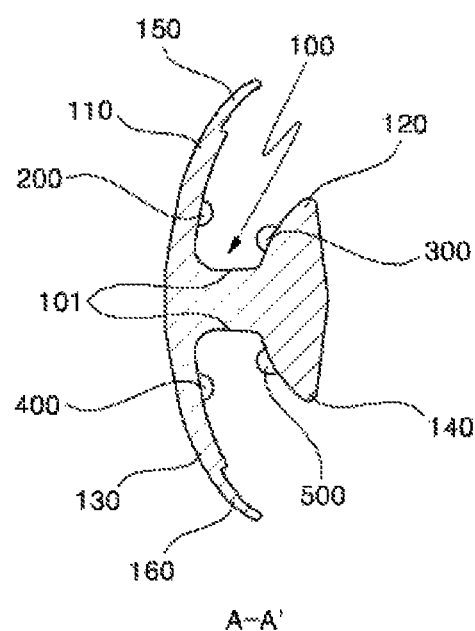
FIG. 6 represents a sectional view cut into the A-A' direction of the horizontal supporting portion in FIG. 4.
Figure 7:
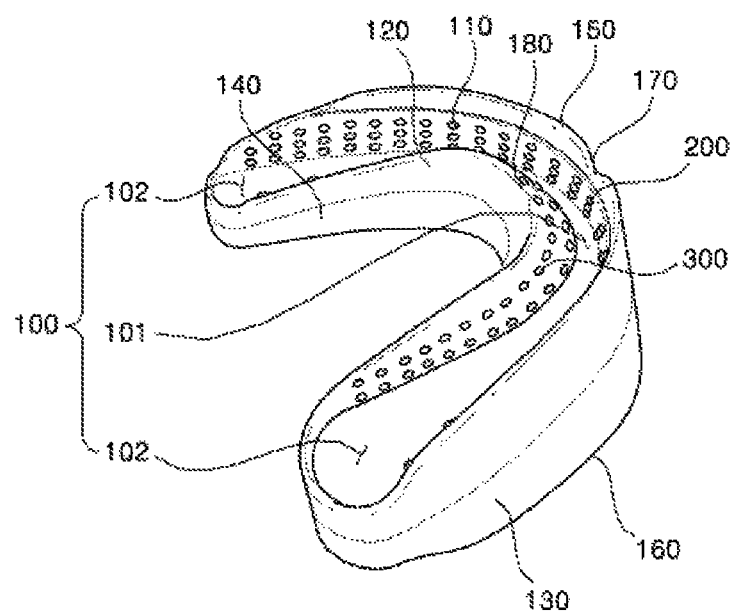
FIG. 7 represents a perspective view of the orthodontics and temporomandibular joint balancing appliance according to another embodiment of the present invention.
Figure 8:
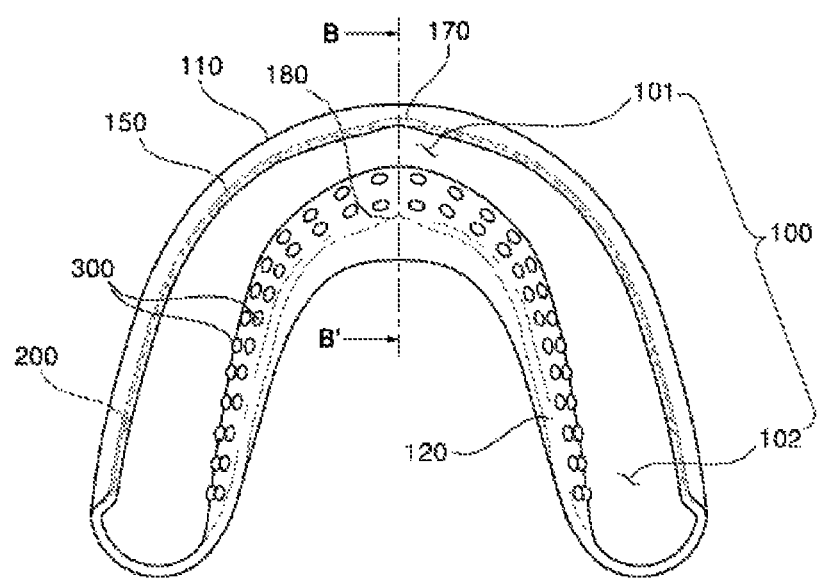
FIG. 8 represents a floor plan of the orthodontics and temporomandibular joint balancing appliance according to another embodiment of the present invention.
Figure 9:
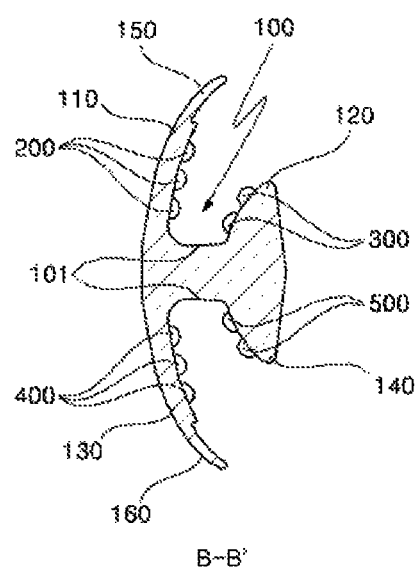
FIG. 9 represents a sectional view cut into the B-B' direction of the horizontal supporting portion in FIG. 8.

FIG. 1 represents a perspective view of the orthodontics and temporomandibular joint balancing appliance according to one embodiment of the present invention, FIG. 2 represents a side view of the orthodontics and temporomandibular joint balancing appliance according to one embodiment of the present invention, FIG. 3 represents a front view of the orthodontics and temporomandibular joint balancing appliance according to one embodiment of the present invention, FIG. 4 represents a floor plan of the orthodontics and temporomandibular joint balancing appliance according to one embodiment of the present invention, FIG. 5 represents a base drawing of the orthodontics and temporomandibular joint balancing appliance according to one embodiment of the present invention, FIG. 6 represents a sectional view cut into the A-A' direction of the horizontal supporting portion in FIG. 4, FIG. 7 represents a perspective view of the orthodontics and temporomandibular joint balancing appliance according to another embodiment of the present invention, FIG. 8 represents a floor plan of the orthodontics and temporomandibular joint balancing appliance according to another embodiment of the present invention, and FIG. 9 represents a sectional view cut into the B-B' direction of the horizontal supporting portion in FIG. 8.

First of all, referring to FIG. 1 and FIG. 2, the orthodontics and temporomandibular joint balancing appliance according to one embodiment of the present invention comprises: a horizontal supporting portion 100 formed as the oral cavity shape, in which upper incisor teeth are accommodated in the upper part and lower incisor teeth are accommodated in the lower part; an upper part outer wall 110, which is extended to the direction perpendicular to an upper part outer rim of the horizontal supporting portion and supports the outer part of the upper incisor teeth; an upper part inner wall 120, which is extended to the direction perpendicular to an upper part inner rim of the horizontal supporting portion and supports the inner part of the upper incisor teeth; a lower part outer wall 130, which is formed along a lower part outer rim of the horizontal supporting portion and supports the outer part of the lower incisor teeth; a lower part inner wall 140, which is formed along a lower part inner rim of the horizontal supporting portion and supports the inner part of the lower incisor teeth; an upper gum protecting portion 150, which is extended from the upper part outer wall toward gum and protects gum; and a lower gum protecting portion 160, which is extended from the lower part outer wall toward gum and protects gum.

In the orthodontics and temporomandibular joint balancing appliance according to one embodiment of the present invention, the horizontal supporting portion 100 is formed as oral cavity shape, U-shape, so as to make the upper incisor teeth be accommodated in the upper part and the lower incisor teeth be accommodated in the lower part, and the anterior teeth 101 and the posterior teeth 102 are formed to a thickness of 1.6 mm, so as to have a certain degree of strength and make the upper incisor teeth and lower incisor teeth enoughly contact to the horizontal supporting portion 100 when occluding teeth. As shown in FIG. 1, the upper part outer wall 110 is extended to the direction perpendicular to the upper part outer rim of the horizontal supporting portion 100, and formed to a certain height, so as to support the outer part of the upper incisor teeth when accomodating upper incisor teeth.

In the orthodontics and temporomandibular joint balancing appliance according to one embodiment of the present invention, the upper part of the horizontal supporting portion 100 is formed to have gentle slope inside according to normal position of the upper incisor teeth, so as to make the upper incisor teeth be comfortly accommodated. According to general shape of teeth, slope angle of the anterior teeth 101 of the horizontal supporting portion 100 formed larger than that of the posterior teeth 102 of the horizontal supporting portion 100. Slope angle of the anterior teeth 101 may be formed gradually smaller toward the posterior teeth 102, and slope angle of the posterior teeth 102 may be formed almost horizontal. Further, left and right sides of the posterior teeth 102 of the horizontal supporting portion 100 may have same thickness, and also left posterior teeth and the right posterior teeth may have different thickness. Preferably, considering step difference between the left molar part and the right molar part, thickness of the right posterior teeth of the horizontal supporting portion 100 may be formed larger than thickness of the left posterior teeth.

According to structural difference of teeth, molars of one side may be occluded earlier to molars of the other side, and the occluded area of one side also may become larger than the area of the other side. Therefore, in the present invention, the part where molars of one side are accommodated is formed thicker than the part where molars of the other side are accommodated, so as to correct delicate structural difference between left and right teeth.

Referring to FIG. 1 to FIG. 6, the anterior teeth 101 of the horizontal supporting portion 100 where incisors are accommodated is formed narrow in the light of width of incisors, so as to tightly fix incisors, and the posterior teeth 102 of the horizontal supporting portion 100 where molars are accommodated is formed wider than incisors. Thus, considering thickness difference between incisors and molars, width may become gradually wider from the anterior teeth 101 to the posterior teeth 102.

The upper part inner wall 120 is extended to the direction perpendicular to the upper part inner rim of the horizontal supporting portion 100. Preferably, as shown in FIG. 6, it may be formed to support inside of upper incisor teeth when accomodating the upper incisor teeth but occupy a certain volume with the cross sectional form of triangular pyramid but not flat.

The lower part outer wall 130 is formed along the lower part outer rim of the horizontal supporting portion 100, and formed to have a certain height, so as to support the outer part of lower incisor teeth when accomodating the lower incisor teeth.

The lower part inner wall 140 is formed along the lower part inner rim of the horizontal supporting portion 100. Preferably, as shown in FIG. 6, it may be formed to support inside of lower incisor teeth when accomodating the lower incisor teeth but occupy a certain volume with the cross sectional form of triangular pyramid but not flat.

The orthodontics and temporomandibular joint balancing appliance of the present invention is characterized that it minimizes foreign body sensation formed between gum and teeth and increases an effect of preventing delicate injury formed at gum when accomodating teeth, by comprising the gum protecting portion, which protects gum.

In the orthodontics and temporomandibular joint balancing appliance of the present invention, as shown in FIG. 6, the upper outer gum protecting portion and the lower outer gum protecting portion 150, 160 are formed to be extended from the upper and lower part outer walls 110, 130 to the direction of gum as leaned outside, and formed thinner than the upper part outer wall and lower part outer wall 110, 130. Accordingly, it may stimulate gum and minimize foreign body sensation formed between gum and upper incisor teeth at the same time, and may increase an effect of preventing delicate injury formed at gum when wearing and removing the orthodontics and temporomandibular joint balancing appliance.

The orthodontics and temporomandibular joint balancing appliance of the present invention is characterized that the upper part outer and inner protrusions 200, 300 and lower part outer and inner protrusions 400, 500 are formed at the upper part outer and inner walls 110, 120 and lower part outer and inner walls 130, 140 as means of fixing the protecting appliance to teeth and stimulating teeth at the same time.

For correcting the temporomandibular joint, it is needed to solve teeth imbalance by protecting teeth from pressure. Accordingly, it is needed to correctly fix an appliance protecting orthodontics and temporomandibular joint to teeth. If the protecting appliance is not correctly fixed to teeth, a reverse effect of straining a temporomandibular joint on the contrary may be produced. Further, continuous stimulation to teeth may be needed.

In the orthodontics and temporomandibular joint balancing appliance of the present invention, the protrusion is formed at least one per tooth, and may play roles of inducing accomodation of teeth while stimulating teeth, and continuously stimulating teeth while minimizing teeth injury by tightly fixing teeth steady.

Referring to FIG. 4, FIG. 5 and FIG. 6, the upper part outer protrusion 200 and the upper part inner protrusion 300 are formed to be protruded at the side faced upper incisor teeth, of the upper part outer wall 110 and the upper part inner wall 120 of the horizontal supporting portion 100, and play roles of preventing removal of the appliance from teeth by blocking generation of space between upper incisor teeth and the upper part outer wall 110 and the upper part inner wall 120 when accomodating the upper incisor teeth, and continuously applying proper stimulation to the upper incisor teeth at the same time.

The upper part outer protrusion 200 or the upper part inner protrusion 300 may be formed at least one per tooth, and the appliance may be possible to comprise only the upper part inner protrusion 300 or the upper part outer protrusion 200, or both of the upper part outer protrusion 200 and the upper part inner protrusion 300.

Further, in the present invention, the lower part outer protrusion 400 and the lower part inner protrusion 500 play a role of a guide inducing accomodation of lower incisor teeth to the temporomandibular joint balancing appliance when charging the lower incisor teeth, and the protrusions protruded from inside and outside of lower incisor teeth play a role of preventing getting out of the lower part of the horizontal supporting portion 100 by tightly fixing the accommodated lower incisor teeth steady. The lower part outer protrusion 400 or the lower part inner protrusion 500 may be formed at least one per tooth, and the appliance may be possible to comprise only the lower part inner protrusion 500 or the lower part outer protrusion 400, or both of the lower part inner protrusion 500 and the lower part outer protrusion 400.

Referring to FIG. 7 to FIG. 9, in the orthodontics and temporomandibular joint balancing appliance according to another embodiment of the present invention, in order to maximize an effect of preventing breakaway of teeth and increase orthodontics effect, the upper part outer protrusion 200 and the lower part outer protrusion 400 are formed to be protruded in column of threes at the sides faced upper incisor teeth and lower incisor teeth, of the upper part outer wall 110 and the lower part outer wall 130 of the horizontal supporting portion 100 of the orthodontics and temporomandibular joint balancing appliance. The upper part inner protrusion 300 and the lower part inner protrusion 500 are formed to be protruded in column of twos at the sides faced upper incisor teeth and lower incisor teeth, of the upper part inner wall 120 and the lower part inner wall 140.

Further, as shown in FIG. 1, the upper gum protecting portion 150 of the orthodontics and temporomandibular joint balancing appliance of the present invention is possible to comprise the first upper part groove 170 in order to protect gum, enhance fixability to teeth and be easily removed. Further, the upper part inner wall 120 is possible to comprise the second upper part groove 180 in order to enhance fixability to teeth and be easily removed.

If the orthodontics and temporomandibular joint balancing appliance of the present invention is distorted or wobbled when wearing or removing the orthodontics and temporomandibular joint balancing appliance, pressure may be applied to teeth or gum. Accordingly, the upper gum protecting portion 150 and the upper part inner wall 120 play a role of dispersing stress generated when wearing or removing by comprising the first upper part groove 170 and the second upper part groove 180.

Shape of the first upper part groove and the second upper part groove is not particularly limited, and preferably, they may be formed at the centers of the upper gum protecting portion 150 and the upper part inner wall 120.

While the invention has been described with respect to the above specific embodiments, it should be recognized that various modifications and changes may be made and also fall within the scope of the invention as defined by the claims that follow.

What is claimed is:

1. An orthodontics and temporomandibular joint balancing appliance consisting of:
   i) a horizontal supporting portion formed as the oral cavity shape, in which upper incisor teeth are adapted to be accommodated in the upper part and lower incisor teeth are adapted to be accommodated in the lower part;
   ii) an upper part outer wall, which is extended to the direction perpendicular to an upper part outer rim of the horizontal supporting portion and is capable of supporting the outer part of the upper incisor teeth;
   iii) an upper part inner wall, which is extended to the direction perpendicular to an upper part inner rim of the horizontal supporting portion and is capable of supporting the inner part of the upper incisor teeth;
   iv) a lower part outer wall, which is formed along a lower part outer rim of the horizontal supporting portion and is capable of supporting the outer part of the lower incisor teeth;
   v) a lower part inner wall, which is formed along a lower part inner rim of the horizontal supporting portion and is capable of supporting the inner part of the lower incisor teeth;
   vi) an upper gum protecting portion, which is extended from the upper part outer wall, wherein the upper gum protecting portion is adapted to extend toward the gum and adapted to protect the gum; and
   vii) a lower gum protecting portion, which is extended from the lower part outer wall, wherein the lower gum protecting portion is adapted to extend toward the gum and adapted to protect the gum,
   wherein the upper part outer wall comprises bump shaped upper part outer protrusions on a side of the upper part outer wall, wherein the bump shaped upper part outer protrusions are adapted to face the upper incisor;
   wherein the upper part inner wall comprises bump shaped upper part inner protrusions on a side of the upper part inner wall, wherein the bump shaped upper part inner protrusions are adapted to face the upper incisor;
   wherein the lower part outer wall comprises bump shaped lower part outer protrusions on a side of the lower part outer wall, wherein the bump shaped lower part outer protrusions are adapted to face the lower incisor;
   wherein the lower part inner wall comprises bump shaped lower part inner protrusions on a side of the lower part inner wall, wherein the bump shaped lower part inner protrusions are adapted to face the lower incisor;
   wherein the upper part outer protrusion or the upper part inner protrusion are formed at the ratio of at least one per tooth; and
   wherein the lower part outer protrusion or the lower part inner protrusion are formed at the ratio of at least one per tooth,
   wherein the bump shaped upper part outer protrusions and the bump shaped lower part outer protrusions are formed to be protruded in only column of threes at the sides faced upper incisor teeth and lower incisor teeth,
   wherein the bump shaped upper part inner protrusions and the bump shaped lower part inner protrusions are formed to be protruded in only column of twos at the sides faced upper incisor teeth and lower incisor teeth,
   wherein the upper part inner wall is formed to support inside of upper incisor teeth when accomodating the upper incisor teeth but has a support surface in the form of curvature, and is formed with a triangular cross sectional area,
   wherein the lower part inner wall is formed to support inside of lower incisor teeth when accomodating the lower incisor teeth but has a support surface in the form of curvature, and is formed with a triangular cross sectional area,
   wherein the upper outer gum protecting portion is formed to be extended from the upper part outer wall to the direction of gum outwardly,
   wherein the lower outer gum protecting portion is formed to be extended from the lower part outer wall to the direction of gum outwardly,
   wherein the upper outer gum protecting portion is formed thinner than the upper part outer wall, wherein the lower outer gum protecting portion is formed thinner than the lower part outer wall,
wherein the upper gum protecting portion comprises a first upper part groove for protecting gum, enhancing fixability with teeth and enabling easier removal,
wherein the upper part inner wall comprises a second upper part groove for enhancing fixability with teeth and enabling easier removal.

* * * * *